United States Patent [19]
Glenn

[11] Patent Number: 5,241,954
[45] Date of Patent: Sep. 7, 1993

[54] NEBULIZER

[76] Inventor: Joseph G. Glenn, Box 91, Broken Arrow, Okla. 74013

[21] Appl. No.: 705,588

[22] Filed: May 24, 1991

[51] Int. Cl.⁵ .................. A61M 11/00; B05B 1/26
[52] U.S. Cl. ..................... 128/200.18; 128/200.21; 239/338
[58] Field of Search ............... 128/200.14, 200.18, 128/200.21, 203.12; 239/335, 338, 354, 370, 419.5

[56] References Cited

U.S. PATENT DOCUMENTS

| | | | |
|---|---|---|---|
| 2,826,454 | 3/1958 | Coanda | 299/88.5 |
| 3,857,909 | 12/1974 | Huggins | 128/200.18 |
| 4,007,238 | 2/1977 | Glenn | 128/200.18 |
| 4,116,387 | 9/1978 | Kremer, Jr. et al. | 128/200.18 |
| 4,251,033 | 2/1981 | Rich et al. | 128/200.18 |
| 4,344,574 | 8/1982 | Meddings et al. | 128/200.18 |
| 4,429,835 | 2/1984 | Brugger et al. | 128/200.18 |
| 4,512,341 | 4/1985 | Lester | 128/200.21 |
| 4,566,451 | 1/1986 | Badewien | 128/200.21 |
| 4,792,097 | 12/1988 | Kremer, Jr. et al. | 128/200.21 |

FOREIGN PATENT DOCUMENTS

| | | | |
|---|---|---|---|
| 0276939 | 8/1988 | European Pat. Off. | 128/200.21 |
| 1198298 | 8/1965 | Fed. Rep. of Germany | 239/338 |
| 2233919 | 1/1991 | United Kingdom | 128/200.21 |

Primary Examiner—Edgar S. Burr
Assistant Examiner—Kimberly L. Asher
Attorney, Agent, or Firm—Head & Johnson

[57] ABSTRACT

A nebulizer which includes a housing having a vertical axis, an open bottom, an air inlet tube extending into the housing and an outlet tube extending from the housing. A bottom cup is removably attached to the open bottom for storing liquid medication, the bottom cup having an opening therethrough. Pressurized air is supplied through the bottom cup opening into the housing and a capillary tube extends from the cup to the air supply so that liquid medication will be drawn up through the capillary tube to form droplets. An axial cylindrical chimney is receivable inside the housing, the chimney having an annular flange extending perpendicularly from the chimney, the flange capable of resting against the housing. The chimney includes a removable check valve at the top thereof. A horizontal target extends across the cylindrical chimney, whereby the air supply and liquid droplets will impinge on the horizontal target and impinge on the check valve, the droplets being broken into micron size droplets for delivery to a patient.

8 Claims, 3 Drawing Sheets

NEBULIZER

BACKGROUND OF THE INVENTION

1. Field of the Invention

The present invention relates to a breathing device for administering a liquid medicant to a patient.

2. Prior Art

Nebulizers or atomizers used with intermittent positive pressure breathing (IPPB) equipment or with the patient's own natural breathing effort have been proven effective as a delivery system for liquid medicant.

A problem with many previous nebulizers is the size and distribution of liquid particles that are produced. Large droplets of medication are trapped on the walls of the mouth or throat, and as such, never pass into the lungs. For the liquid medication to reach the smaller passages in the bronchial tubes and lungs, the size of the liquid particles must be below 5 microns. At one time, an average particle size under 5 microns was acceptable. Increasingly, however, an even smaller average particle size is being called for by the medical community with certain medications and for certain treatments. Additionally, the actual particle count delivered is of great importance.

A further problem associated with many nebulizers is that they are not directly responsive to the increase or decrease in the patient's breathing. When a patient inhales, he or she is typically inhaling at a rate from 15 to 50 liters per minute. The output of most nebulizers drops off dramatically when a patient inhales at a rate exceeding 20 liters per minute.

In the present invention, all of the air inhaled by the patient is directed past the saturated mist. As the air flow to the patient's lungs is increased, additional liquid particles are delivered to the lungs. Conversely, when the air flow to the patient's lungs is decreased, the number of liquid particles is decreased. Thus, the amount of saturated air delivered to the patient is directly responsive to the increase or decrease in the patient's breathing.

Applicant is aware of a number of prior art patents including Glenn (U.S. Pat. No. 4,007,238) and Lester (U.S. Pat. No. 4,512,341).

The Lester nebulizer is connected to a breathing apparatus to allow entry of atmospheric air. The nebulizer is connected to a "T" in the air supply line. As the patient breathes in, additional atmospheric air is drawn into the lungs. The amount of saturated air, however, does not change in response to the patient's breathing.

Applicant's prior patent (U.S. Pat. No. 4,007,238) solved the problem and provides responsiveness to the patient's breathing. A significant number of improvements, however, has been made and are included in the present invention.

An additional baffle system has been provided in the present invention which serves to further reduce the average particle size delivered. The baffling may be added as an option to the nebulizer and may be removed, if desired. The additional baffle system may take a number of configurations and is interchangeable depending on the particular medication and treatment prescribed.

Additionally, the present invention has a design which more evenly distributes the atmospheric air which passes through the chimney and mixes with the saturated mist. The ability to provide a thoroughly saturated mist is, thus, enhanced.

It is a principal object and purpose of this invention to provide a nebulizer which, with a supply of pressurized air, will produce a fine mist of liquid droplets of extremely small size.

It is further object and purpose of the present invention to provide a nebulizer with a removable baffling system to vary the size of liquid particles.

SUMMARY OF THE INVENTION

The nebulizer of the present invention includes an outer cylindrical housing having a longitudinal axis vertically arranged. The housing has a closed top and an open bottom.

An atmospheric air inlet extends through a side wall of the cylindrical housing. An outlet tube extends from an opening in the cylindrical housing substantially opposite of the inlet tube.

The lower portion of the housing has a slightly larger diameter than the upper portion of the housing. The lower portion and the upper portion are connected together by a sloping shoulder.

Concentrically received within the housing is a chimney open at both ends. The chimney has an extending annular flange which rests against the sloping shoulder. The open bottom of the housing is closed by a medication cup removably attached.

An opening through the bottom of the cup contains a tube which terminates interior to the nebulizer at an orifice located above the upper level of the liquid medication.

Mounted near and above the orifice is a capillary housing including a capillary tube extending from a point near the orifice downward into the liquid medication. During operation, a stream of pressurized air flowing through the orifice causes induction of liquid medication from the cup through the capillary tube where the liquid droplets are moved at high velocity into the chimney and strike a cylindrical target extending horizontally across the cylindrical chimney.

Atmospheric air entering the nebulizer travels downward toward the lower opening of the chimney. Additionally, atmospheric air from the air inlet passes through an opening in the horizontal target extending across the chimney. Atmospheric air which exits the horizontal target also travels downward toward the bottom opening of the chimney.

An additional, removable baffle is provided at the top of the chimney. A valve holder has a somewhat flexible body that may be force fit into the top opening of the chimney or may be fabricated as a part of the chimney.

The valve holder has an upwardly extending post upon which may be placed a flexible membrane acting as a one-way check valve to allow the mist to exit from the chimney into the housing.

The fine mist of liquid particles which exits from the chimney into the housing and will then pass into outlet tube, and then to the patient. Any larger liquid droplets which fall out will descend to the annular flange, which is provided with an opening. The liquid droplets will, thereby, return to the medication cup.

DETAILED DESCRIPTION OF THE PREFERRED EMBODIMENTS

Figure 1:
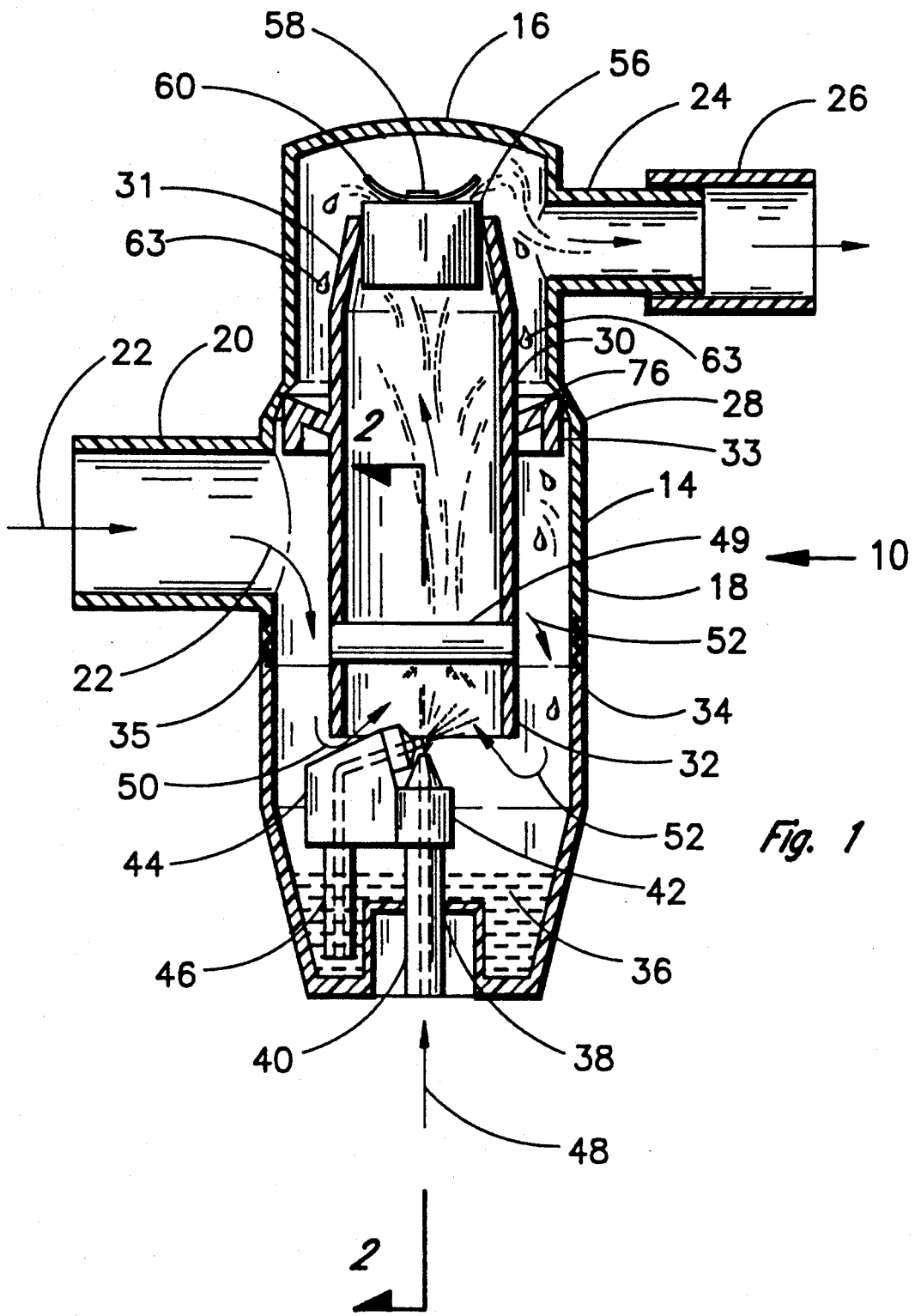
FIG. 1 is a cross-sectional view of a nebulizer constructed in accordance with the present invention.

Referring to the drawings in detail, FIG. 1 illustrates a cross-sectional view of a nebulizer 10 constructed in accordance with the present invention.

The nebulizer 10 includes an outer cylindrical housing 14 which is normally positioned upright with its longitudinal axis vertically arranged. While the present embodiment has a cylindrical housing, it will be understood that other forms might also be utilized. The cylindrical housing 14 has a closed top 16 and an open bottom 18.

An atmospheric air inlet 20 extends through a sidewall of the cylindrical housing 14. Arrows 22 show the direction of atmospheric air which is allowed to pass through the inlet tube and into the housing 14. An outlet tube 24 extends from an opening in the cylindrical housing. The outlet tube 24 is substantially opposite the inlet tube 20; other configurations, however, are possible. For instance, the outlet 24 may extend upward vertically from the housing 14. A removable mouthpiece 26 may extend from the outlet tube 24.

The lower portion of housing 14 has a slightly larger diameter than the upper portion of the cylindrical housing. Where the lower portion meets the upper portion, the housing narrows to form a sloping shoulder 28.

Concentrically positioned and received within the housing 14 is a cylindrical chimney 30 which is open at both ends—the top end 31 and bottom end 32. The chimney has an extending annular flange 33 which extends perpendicularly from the exterior of the cylindrical wall of the chimney. When installed, the chimney is inserted in the open bottom 18 and the annular flange rests against the inside cylindrical wall of the housing 14 at sloping shoulder 28. The annular flange fits snugly against the lower portion. As will be observed, the chimney 30 is removable from the housing and may be of different configurations.

With the chimney so installed, an annulus is formed between the housing and the chimney.

The open bottom of the housing 14 is closed by a medication cup 34 which is removably attached to the housing, in this case by means of threads 35. The cup is closed at the bottom for storing a dosage of liquid medication 36 therein. When the bottom cup is attached, a closed chamber is formed with the exception of the inlet tube 20 and the outlet tube 24.

An opening 38 through the bottom of the cup 34 contains a vertical tube 40 which extends through the cup. The tube 40 terminates interior to the nebulizer 10 at an orifice 42 located above the upper lever of the liquid medication 36. During operation of the nebulizer, a stream of pressurized air is provided through the tube 40 and orifice 42 and into the closed chamber of the nebulizer formed by the housing 14 and cup 34.

Mounted near and above the orifice 42 is a capillary housing 44. The capillary housing includes a capillary tube 46 extending from a point near the orifice 42 downward into the liquid medication 36. During operation, the stream of pressurized air indicated by arrow 48 flowing through the orifice 42 will cause induction of liquid medication from the cup 34 through the capillary tube 46 where the liquid droplets will be moved at high velocity into the housing 14.

It will be recognized that other capillary mechanisms might be used to draw liquid up to the stream of pressurized air.

The open bottom 32 of the chimney 30 is located above the pressurized air orifice 42 and capillary housing 44. Accordingly, the liquid droplets and pressurized air will move at high velocity into the chimney. A cylindrical target 49 extends horizontally across the cylindrical chimney.

During operation of the nebulizer 10, intermittent air flow is created by the patient's breathing. Atmospheric air enters the nebulizer through air inlet 20 as seen by arrows 22. The atmospheric air will travel in two directions once inside the housing. It will travel downward and toward the lower opening of the chimney as seen by arrow 50. Additionally, atmospheric air will pass through an opening 51 in the horizontal target extending across the chimney as seen by arrows 52. Air which exits the horizontal target will then travel downward toward the bottom opening 32 of the cylindrical chimney. By use of the opening in the horizontal target, atmospheric air is more evenly distributed in the housing. The air flow will then be directed upward through the interior of the chimney.

Figure 2:
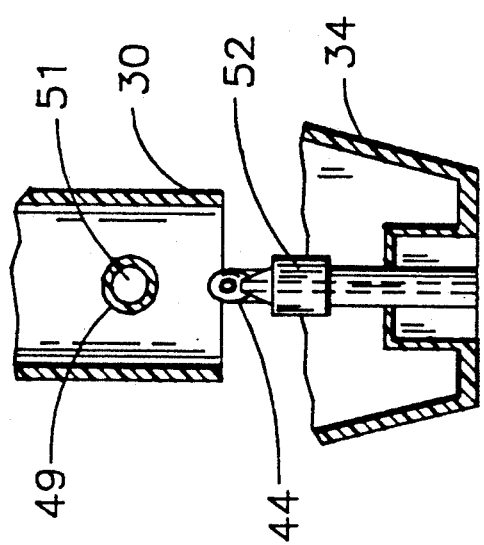
FIG. 2 is a sectional view taken along line 2—2 of the nebulizer as shown in FIG. 1.

The horizontal target and opening 51 therethrough may be observed in the sectional view seen in FIG. 2.

The stream of pressurized air exiting from the orifice 42 and liquid droplets from the capillary tube will, thus, be caused to impinge against horizontal target 49.

It will be observed that the fine mist being produced by the capillary orifice and horizontal target is mixed and swept along with the atmospheric air. This mixture of air and mist then passes upward into the upper portion of the chimney.

Figure 3:
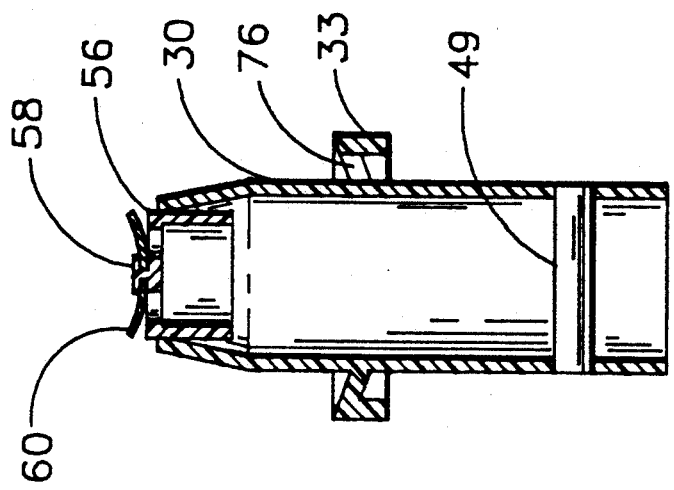
FIG. 3 is a sectional view of one embodiment of a chimney utilized as part of the nebulizer shown in FIG. 1.

An additional, removable baffle mechanism is provided at the top 31 of chimney 30. A valve holder 56 has a somewhat flexible body that may be force fit into the top opening 31. The valve holder might alternatively be fabricated as a part of the chimney 30. The valve holder may have a number of cross baffles, as best seen in the cross-sectioned view in FIG. 3.

The valve holder has an upwardly extending post 58 upon which may be placed a flexible membrane 60. The membrane acts as a one-way check valve to allow the mist to exit from the chimney into the housing 14. As the patient inhales, the valve membrane lifts to allow the mist to pass from the chimney. The use of the valve holder and membrane 60 acts as a secondary baffling system and restricts some of the larger particles from passing to the outlet tube 24.

It has been found that by use of the additional baffle mechanism, namely the valve holder and check valve, the average particle size is reduced significantly. The average particle size may, thus, be controlled by installation and removal of the membrane and valve holder as dictated by the particular medication and treatment prescribed.

Tests by an independent laboratory support the applicant's claim to a dramatic decrease in average particle size by use of a secondary baffling system.

By placing this additional baffle mechanism in the chimney, larger droplets will be knocked out and will descend, returning to the medication cup.

Figure 4:
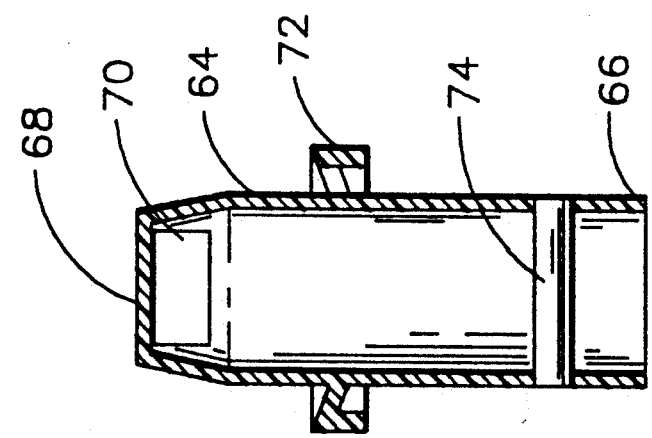
FIG. 4 is an alternate embodiment of a chimney to be utilized with a nebulizer as shown in FIG. 1.

FIG. 4 illustrates an alternate embodiment of a cylindrical chimney 64 for use in the housing 14. The chimney 64 is open at the bottom 66. A top 68 extends horizontally across the chimney 64 with a pair of openings 70 in the cylindrical chimney.

The top 68 of the chimney 64 acts as an additional target against which the liquid particles will impinge. Accordingly, the larger size particles will fall out and be prevented from passing to the outlet tube 24.

The chimney 64, likewise, has an annular flange 72 extending therefrom which will rest against the sloping shoulder 28. The chimney 64 would also include a horizontal target 74 extending across the cylindrical chimney 64.

It will be appreciated that chimney 64 is interchangeable with chimney 30. Accordingly, not only may the chimney 30 be used with or without the valve holder 56 and membrane 60, but the chimney 30 may be replaced with chimney 64.

Returning to a consideration of FIG. 1, the fine mist of liquid particles which exits from the chimney 30 into the housing will pass into outlet tube 24 and then to the patient (not shown). Any larger droplets 63 which condense and fall out will descend to the flange 33, which is provided with a drain opening 76. The droplets will thereby return to the medication cup.

Figure 5:
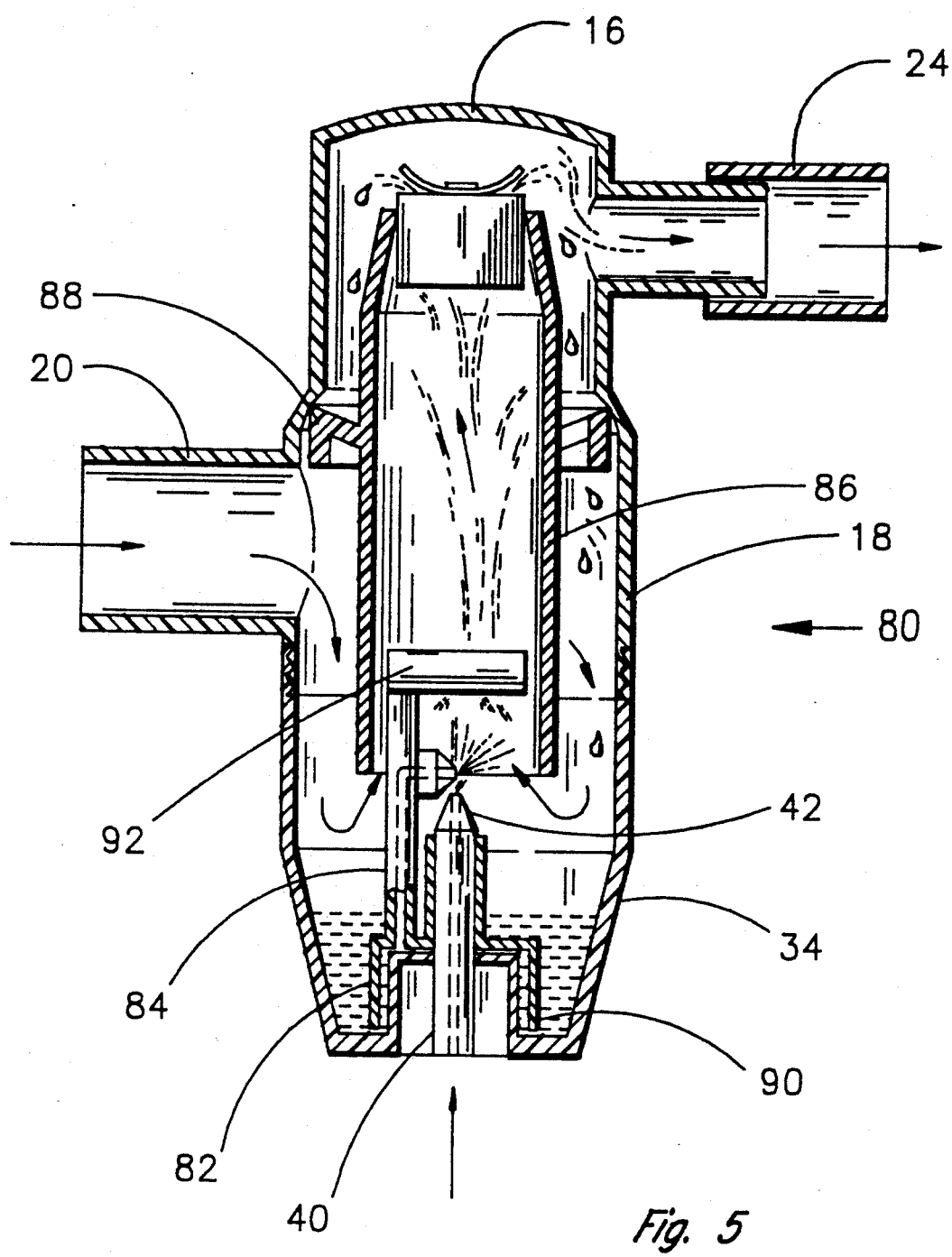

FIG. 5 illustrates an alternate embodiment 80 of the nebulizer having a modified capillary housing 82 and capillary tube 84 and having a modified chimney 86.

As in the other embodiment, the cylindrical housing 14 has a closed top 16 and an open bottom 18. Atmospheric air inlet 20 extends through a sidewall of the cylindrical housing 14. An outlet tube 24 extends from an opening in the cylindrical housing 14 substantially opposite the inlet tube.

The chimney 86 is inserted in the open bottom 18 and an annular flange 88 extending from the chimney rests against the inside wall of the housing.

The open bottom of the housing 14 is closed by a medication cup 34.

With a single capillary tube 46, as seen in FIG. 1, the medication cup 34 could be tipped at an angle and a portion of the medication would remain in the cup 34 and not be drawn into the tube. A salient advantage may be observed from the design of the capillary housing 82. In the present embodiment, the capillary housing 82 has a cylindrical lower end 90 which terminates near the bottom of the medication cup 34. Accordingly, no matter what direction the housing 14 is tipped, medication will be drawn in the capillary housing 82. While this feature is achieved in other nebulizers through use of a coaxial jet, the present embodiment retains use of a capillary tube 84 which is more efficient than a coaxial jet since it can be operated at lower pressurized air rates.

The capillary tube 84 is in fluid communication with the capillary housing 82 so that medication is drawn therein. The capillary tube extends up to the orifice 42 of the tube 40. During operation, the stream of pressurized air flowing through the orifice 42 will cause induction of liquid medication from the medication cup 34, through the capillary housing 82 and through the capillary tube 84 where the liquid droplets will be moved at high velocity into the housing 14.

A cylindrical target 92 extends from the capillary housing 82 and is located above the orifice 42. The stream of pressurized air exiting from the orifice 42 and the liquid droplets from the capillary tube 84 will, thus, be caused to impinge against horizontal target 92.

It will be observed that the horizontal target 92 of the present embodiment 80 is not attached to the chimney 86 but extends from the capillary housing 82.

Any of the previously described secondary baffle mechanisms might be employed.

Whereas, the present invention has been described in relation to the drawings attached hereto, it should be understood that other and further modifications, apart from those shown or suggested herein, may be made within the spirit and scope of this invention.

What is claimed is:

1. A nebulizer which comprises:
   a. a housing having a vertical axis, said housing having an open bottom, an air inlet tube extending into said housing, and an outlet tube extending from said housing;
   b. a bottom cup removably attached to said open bottom for storing liquid medication therein, said bottom cup having an opening therethrough;
   c. means to supply air under pressure through said bottom cup opening into said housing;
   d. capillary tube means extending from said bottom cup to said air supply means so that said liquid medication will be drawn up through said capillary tube means to form droplets;
   e. an axial cylindrical chimney inside said housing having an annular flange extending from said chimney, said flange resting against said housing, said chimney having removable check valve means at the top thereof, said flange having at least one drain opening permitting communication between fluid exiting said check valve and said cup;
   f. horizontal target means perpendicular to said chimney axis for impingement of said air supply and said liquid droplets on said horizontal target means and on said check valve means, said droplets being broken into smaller micron size droplets by the impingement for delivery to a patient; and
   g. means for removing remaining larger liquid droplets exiting from said check valve means by force of gravity, said larger droplets passing through said at least one drain opening in said chimney flange and back to said bottom cup at all times exterior to said chimney.

2. A nebulizer as set forth in claim 1 wherein said housing is cylindrical and includes a closed top.

3. A nebulizer as set forth in claim 1 wherein said check valve means includes a valve holder removably received in an open top of said axial cylindrical chimney and a flexible valve membrane removably received on said valve holder.

4. A nebulizer as set forth in claim 1 wherein said horizontal target means extends across said cylindrical chimney.

5. A nebulizer as set forth in claim 4 wherein said horizontal target means includes a passageway therethrough to conduct atmospheric air from said air inlet tube.

6. A nebulizer as set forth in claim 5 wherein said horizontal target means includes a passageway therethrough to conduct atmospheric air from said air inlet tube.

7. A nebulizer which comprises:
   a. a housing having a vertical axis, said housing having an open bottom, an air inlet tube extending into said housing, and an outlet tube extending from said housing;

b. a bottom cup removably attached to said open bottom for storing a supply of liquid medication therein, said bottom cup having an opening therethrough;
c. means to supply air under pressure through said bottom cup opening into said housing;
d. capillary tube means extending from said bottom cup to said air supply means so that said liquid medication will be drawn up through said capillary tube means to form droplets;
e. an axial cylindrical chimney inside said housing having an annular flange extending from said chimney and resting against said housing, means to decrease the size of said liquid droplets through impingement and circuitous flow, said means including a closed top for impingement and openings in said cylindrical chimney near said top; and
f. horizontal target means extending across said cylindrical chimney substantially perpendicular to said chimney axis for impingement of said air supply and said liquid droplets on said horizontal target means, said droplets being broken into smaller micron size droplets.

8. A nebulizer which comprises:
a. a housing having a vertical axis, said housing having an open bottom, an air inlet tube extending into said housing, and an outlet tube extending from said housing;
b. a bottom cup removably attached to said open bottom for storing a supply of liquid medication therein, said bottom cup having an opening therethrough;
c. means to supply air under pressure through said bottom cup opening;
d. capillary means extending from said bottom cup to said air supply means so that said liquid medication will be drawn up through said capillary means to form droplets;
e. an axial cylindrical chimney inside said housing having an annular flange extending from said chimney and resting against said housing;
f. horizontal target means extending across said cylindrical chimney perpendicular to said chimney axis and having a passageway therethrough;
g. means to conduct and distribute atmospheric air through said passageway from said air inlet tube in said housing, in order to evenly and thoroughly mix atmospheric air in said housing, wherein said air under pressure and said liquid droplets impinge on said horizontal target means, and said droplets are broken into smaller micron size droplets.

* * * * *